United States Patent
Rich

(10) Patent No.: US 6,200,025 B1
(45) Date of Patent: Mar. 13, 2001

(54) FLEXIBLE AUTOMATED SPECIFICATION TESTING FOR QUALITY CHECKS

(75) Inventor: Lawrence A. Rich, Walnut Creek, CA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/212,879

(22) Filed: Dec. 15, 1998

(51) Int. Cl.[7] ....................................................... H05G 1/26
(52) U.S. Cl. ............................. 378/207; 378/65; 702/183
(58) Field of Search .................................. 378/65, 207, 4, 378/118, 117; 702/208, 183; 371/20.1

(56) References Cited

U.S. PATENT DOCUMENTS

| | | | |
|---|---|---|---|
| 4,853,946 | * 8/1989 | Elliott et al. .......................... | 378/207 |
| 5,384,699 | 1/1995 | Levy et al. ............................ | 702/183 |
| 5,608,650 | 3/1997 | McClendon et al. ................. | 702/114 |

FOREIGN PATENT DOCUMENTS

WO 97/42522 A1  11/1997  (WO).

OTHER PUBLICATIONS

WPI Acc. No. 99–431 & DE 19 802 572 A1 (Siemens Health Systems() published Aug. 5, 1991, see Abstract.

WPI Acc. No. 98–256 792 & JP 10 083 315 A (Thosiba) published Mar. 31, 1998, Abstract.

* cited by examiner

*Primary Examiner*—David V. Bruce
*Assistant Examiner*—Drew A. Dunn

(57) ABSTRACT

A system and method for maintaining a network of multiple radiation devices, such as linear accelerator radiation therapy devices. Automated specification testing and checking of the network of radiation therapy devices facilitates integrated analysis of collected information and system calibration. A network interface is provided for coupling the radiation devices to the network through dedicated personal computers (PCs). Databases of device history records and device specifications are maintained on a system calibration server for each of the multiple radiation devices. Dosimetry scanners operable with the radiation devices use a dedicated PC as a client user interface in communication with the server via the network and one radiation device. The radiation devices are responsive to the client user interface for undergoing an operation sequence with dosimetry scanner performing a series of tests. The radiation device is thus operated automatically via the PC client user interface in accordance with the series of tests performed by the dosimetry scanner. The dedicated PCs and any additional PCs on the network have read-only access to server database information.

20 Claims, 10 Drawing Sheets

FLEXIBLE AUTOMATED SPECIFICATION TESTING FOR QUALITY CHECKS

RESERVATION OF COPYRIGHT

A portion of the disclosure of this patent document contains material which is subject to copyright protection. The copyright owner has no objection to facsimile reproduction by anyone of the patent document or the patent disclosure as it appears in the Patent and Trademark Office patent file or records, as it becomes available to the public, but otherwise reserves all copyright rights whatsoever.

BACKGROUND OF THE INVENTION

1. Field of the Invention

The present invention relates to calibration of radiation devices, and more particularly to the automated specification testing, checking and calibration of radiation therapy devices for use in the oncology field.

2. Description of the Related Art

System calibration methods presently in use for specification testing, checking and calibration of radiation devices are cumbersome and error prone. In such known systems, measurement data is typically recorded by hand and is reviewed several times to verify the accuracy and completeness of the data. Scan data collection is accomplished through manual control of the radiation therapy devices using scanning equipment which requires each scan to be manually initiated.

The radiation therapy device settings are manually keyed into the scanning equipment software, and verification of the data entry is accomplished through a review of the scan printouts. Finally, the results of the analysis of the scan are manually recorded. The scenario outlined above applies to most clinical setting. Similar tasks are performed on a routine basis to verify proper operation of the radiation therapy devices.

A system calibration department of a medical device manufacturer is typically responsible for verifying that the radiation therapy device interlocks are operational and calibrated according to various machine parameters to ensure that the therapy device meets all performance specifications. The work performed by the system calibration department is documented in the DHR. The section of the DHR completed currently includes several pages that are filled out by hand. This procedure used may be broken into two main sections, pre-test and the radiation test.

The various machine interlocks are tested as part of the pre-test section. Typically a fault condition is simulated and the test technician verifies that an interlock trips. The fault condition is then removed and the test technician verifies that the interlock clears. The test technician then records his initials and the date in the appropriate section of the DHR.

The radiation test consists of testing to ensure that the machine meets its performance specifications. Several components of the radiation therapy devices need to be aligned as part of this procedure. These include the bending magnet, defining head jaws, flattening filters, and the light field. Typically rough scans are performed and adjustments are made to correct any alignment errors. Once the alignment is correct, a series of final scans are made and recorded as part of the DHR to document the machine performance. There are also several machine parameters that are calibrated as part of this procedure. These parameters affect the stability and intensity of the beam. They are calibrated using external equipment, such as oscilloscopes, multi-meters, and the scanning equipment. Once the alignment and calibration is complete, any remaining performance specifications are tested to ensure that the machine is operating properly. These include specifications such as rotational treatments and leakage measurements. Machine configuration information, machine parameters, and test equipment used are recorded as part of the DHR.

To this end, it would be desirable to provide a system for automatically collecting all information required for the device history records, which allows the information to be stored in a database. It would be further desirable to eliminate the human user interface in a calibration and testing system while performing a number of tests on the radiation devices. Accordingly, after the radiation device being tested is turned on by the user, the system may then perform the necessary programming via a communications network to carry out a series of tests and calibration checks. Accordingly, the package should allow the technicians to quickly and accurately record all data required for machine calibration, and allow information to be available on the company intranet or the like for access from remote locations.

SUMMARY OF THE INVENTION

In a described embodiment, linear accelerator based radiation therapy devices may be programmed via a communications network to facilitate automated specification testing, checking, calibration and integrated analysis of radiation therapy devices. Information is collected from individual radiation devices using dosimetry scanners operable with a client user interface in communication with a system calibration server. The radiation therapy devices are responsive to the client user interface for undergoing an operation sequence with dosimetry scanner performing a series of tests.

The radiation device may be operated automatically via the network in accordance with the series of tests performed by the dosimetry scanner. Document templates retrievable with the client user interface may be used for creating the device history records for the radiation devices. The document templates provide a user interface format including check lists, prompting, semi-automatic or automatic information collection with the radiation device undergoing operation sequences without manual activation of the radiation device by the user. Programming of the radiation device in the operation sequence of the testing commands is generated in accordance with a plurality of tests performed by the dosimetry scanner during which the radiation device may generate radiation.

The design of the system allows quality assurance data to be collected efficiently and accurately. This is accomplished through verification of manual data entry, automated control of the scanning equipment, automated analysis of the data collected by the scanning equipment and integrated control of the radiation therapy devices. The design also provides the flexibility to make changes to the data format easily through the use of document templates. A DHR template located on the server is used to create all new DHRs, allowing changes to the DHR format to be quickly and easily implemented. When a DHR is completed, the package notifies Document Control and the database becomes "frozen," disallowing any further modifications.

The automation capabilities offered by the described software package provide integrated control of both the radiation therapy devices and the scanning equipment, as well as automated analysis capabilities. This allows scan sequences to be performed automatically with verification of analysis results after each scan. It also allows data to be collected efficiently and consistently. Template based data layout allows the package to be used in various applications without modification. Modular design allows additional functionality to be added as needed for custom applications to collect all information that would normally be provided as part of the DHR.

DHR information is stored in a database located on the system calibration server, which allows technicians to quickly and accurately record all data required for machine calibration. The data may be made available on the company intranet allowing users to access the information from remote locations. A DHR template located on the server may be used to create all new DHRs to facilitate changes in the format to be quickly and easily implemented. A separate database is maintained for each DHR, and completed DHRs can be archived regularly.

Briefly summarized, the present invention relates to a system and method for automated specification testing and checking using integrated analysis of collected system calibration information. A network interface couples the radiation devices to the network, and databases of device history records and device specifications are maintained on a system calibration server for each of the multiple radiation devices. Dosimetry scanners operable with the radiation devices use a client user interface in communication with the server and the radiation device via the network. The radiation devices are responsive to the client user interface for undergoing an operation sequence with dosimetry scanner performing a series of tests in accordance with the series of tests performed by the dosimetry scanner.

These and other objects and advantages are realized with automated specification testing and checking of radiation devices. The appended claims set for the features of the present invention with particularity. The invention, together with its objects and advantages, may be best understood from the following detailed description taken in conjunction with the accompanying drawings.

DETAILED DESCRIPTION OF THE INVENTION

Figure 1:
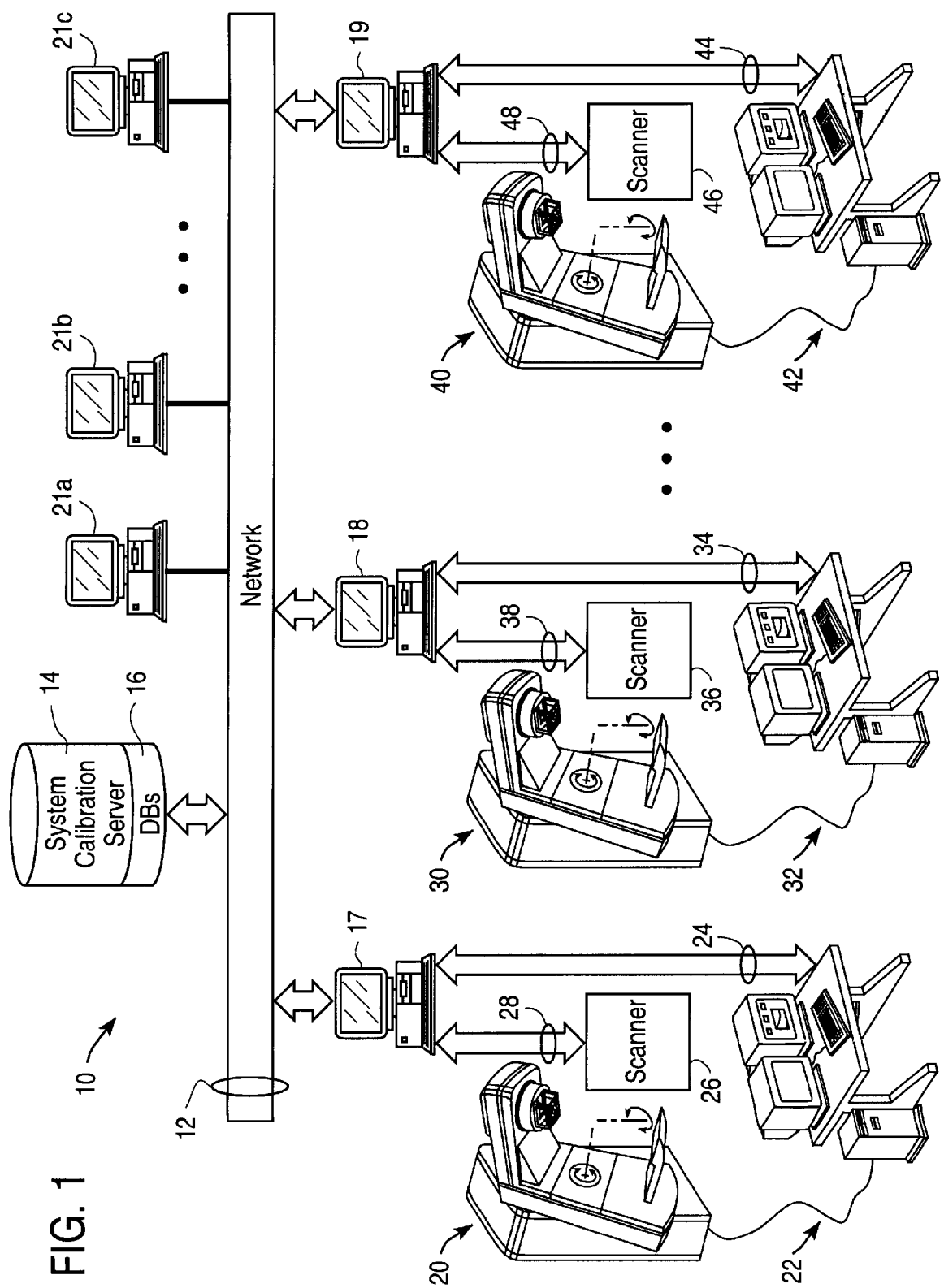
FIG. 1 shows a block diagram of a system for automated specification testing and checking of radiation devices in accordance with the present invention.

As depicted in FIG. 1, a calibration system 10 in accordance with the invention is shown including a network 12 of multiple radiation therapy devices 20, 30 and 40. As discussed further below, a system calibration server 14 uses a database 16 of device history records (DHRs) for each of the multiple radiation therapy devices 20, 30 and 40. The system calibration server 14 also uses the database 16 for device specifications for each of the multiple radiation therapy devices 20, 30 and 40. The system calibration server 14 is a network server for the device history records database the said device specifications database for use with client applications. A multiplicity of dosimetry scanners 26, 36 and 46, typically embodied within the radiation therapy devices 20, 30 and 40, are operable with at least one of each of the radiation therapy devices 20, 30 and 40. Several dedicated personal computers (PCs) 17, 18 and 19 may be provided with client user interfaces in communication between the system calibration server 14 and one each of the radiation therapy devices 20, 30 and/or 40 and respective dosimetry scanners 26, 36 and/or 46 via the network 12, responsive to the client user interface for undergoing an operation sequence. The dosimetry scanners 26, 36 and 46 thus perform a series of tests in accordance with system calibration and maintenance requirements. Additionally, a number of other PCs 21a,b,c may be provided as another client user interface via the network 12 which provides read-only access to server database information.

The radiation therapy devices 20, 30 and 40 are provided as treatment apparatus representative of, for example, the Mevatron™ series of machines available from Siemens Medical Systems, Inc. Such radiation treatment apparatus include a treatment unit 22, 32 and 42 which provide control over the radiation devices for use in the course of therapeutic treatment. Herein, a linear accelerator is located in the gantry of the radiation devices 20, 30 and 40 to generate the high powered radiation required for the therapy. Electron, photon or any other detectable radiation may also be used for the therapy.

A network interface is provided for coupling the radiation devices 20, 30 and 40 to the network 12, in which a first communications link 24, 34 and 44 provides data communications to and from each of the respective radiation devices for receiving commands for carrying out operation sequences. A second communications link 28, 38 and 48 provides communications to and from each of the respective dosimetry scanners 26, 36 and 46 for receiving commands for performing the series of tests on the associated radiation devices 20, 30 and 40 by the dosimetry scanners 26, 36 and 46. The first communications link 24, 34 and/or 44 may be used for automatic sequencing of the radiation device. The second communications link 28, 38 and/or 48 may be provided as a serial interface to dosimetry scanners 26, 36 and 46. The specifications for the interface to the dosimetry scanners 26, 36 and 46 are based on the WP600 Hardware by the Wellhofer company of Schwarzenbruck, Germany. A commercially available scanner control software package, the Buddelship module, disposed in the personal computers associated with each unit provides automated control of dosimetry scanning equipment, herein Wellhofer scanners, allowing for automated analysis of the data collected by scanning equipment with integrated control of the Mevatron. A "Mevatron Module" discussed below is also provided as part of the commercially available Siemens system software for controlling the Mevatron linear accelerator.

The software package describe herein is referred to as the "FAST-Check" package which is used with the system calibration server 14 in the system 10 to provide database storage for DHRs that are currently active. As described further below, the FAST-Check software package facilitates efficient and accurate collection of quality assurance data through verification of manual data entry, automated control of the scanning equipment, automated analysis of the data collected by the scanning equipment and integrated control of the radiation therapy devices. The design also provides the flexibility to make changes to the data format easily through the use of DHR document templates.

An open database connectivity (ODBC) approach to the database connection allows the package to support multiple database vendors. Thus, custom reports can be easily generated using tools provided by the database vendor. DHR information is stored in a database located on the system calibration server, which allows technicians to quickly and accurately record all data required for machine calibration. The data may be made available on the company intranet, allowing users to access the information from remote locations or even over the internet in an encrypted format to maintain security. A DHR template located on the server is used to create all new DHRs, allowing changes to the DHR format to be quickly and easily implemented. When a DHR is completed, the package notifies document control and the database becomes frozen, disallowing any further modifications. Completed DHRs can be archived regularly, and if it is necessary to make any corrections system approval may be required. A separate database is maintained for each DHR.

Data collected as part of the DHR can be divided into four main types: 1) checklist items, 2) measurements made by hand, 3) measurements made using automated systems, and 4) measurements made using automated systems that require user control (i.e. leakage measurements). All four types of data can be collected using the FAST-Check package. The initials of the technician and the date are automatically entered for all types of data, eliminating repetitive entry. Checklist items become check boxes that indicate if an item is complete. Measurements made by hand have rudimentary data verification performed, minimizing the possibility of typographical errors. Measurements made using automated systems have the data automatically entered into the DHR, eliminating the possibility of typographical errors. Measurements made with automated systems that require user control are simplified, and the data is automatically entered into the DHR, eliminating the possibility of typographical errors. Perhaps most importantly, all data must be filled in to complete the DHR, ensuring that there are no items left blank.

Whereas, traditionally control of the scanning equipment and analysis of the scans have been provided by the equipment vendor, the modules provided as part of FAST-Check allow changes to be easily and quickly implemented. They also allow for much better control over how the infirmation is collected, eliminating differences in technique between technicians and allowing analysis results to be automatically entered into the DHR.

The system design for FAST-Check is in response to the need to quickly and efficiently collect the data required for the DHR, while maintaining the flexibility to make changes to the DHR format easily, with minimal maintenance requirements for the system. In meeting these requirements, the following design objectives include allowing information to be exchanged with the radiation therapy devices; support for performing rough scans required for beam alignment and flattening filter alignment; ease of installation/configuration; system and application designed with long term flexibility. The System Calibration Architecture may be divided into four main subsystems, the radiation therapy device control console, the scanning equipment, the System Calibration Server, and the FAST-Check Subsystem.

Figure 2:
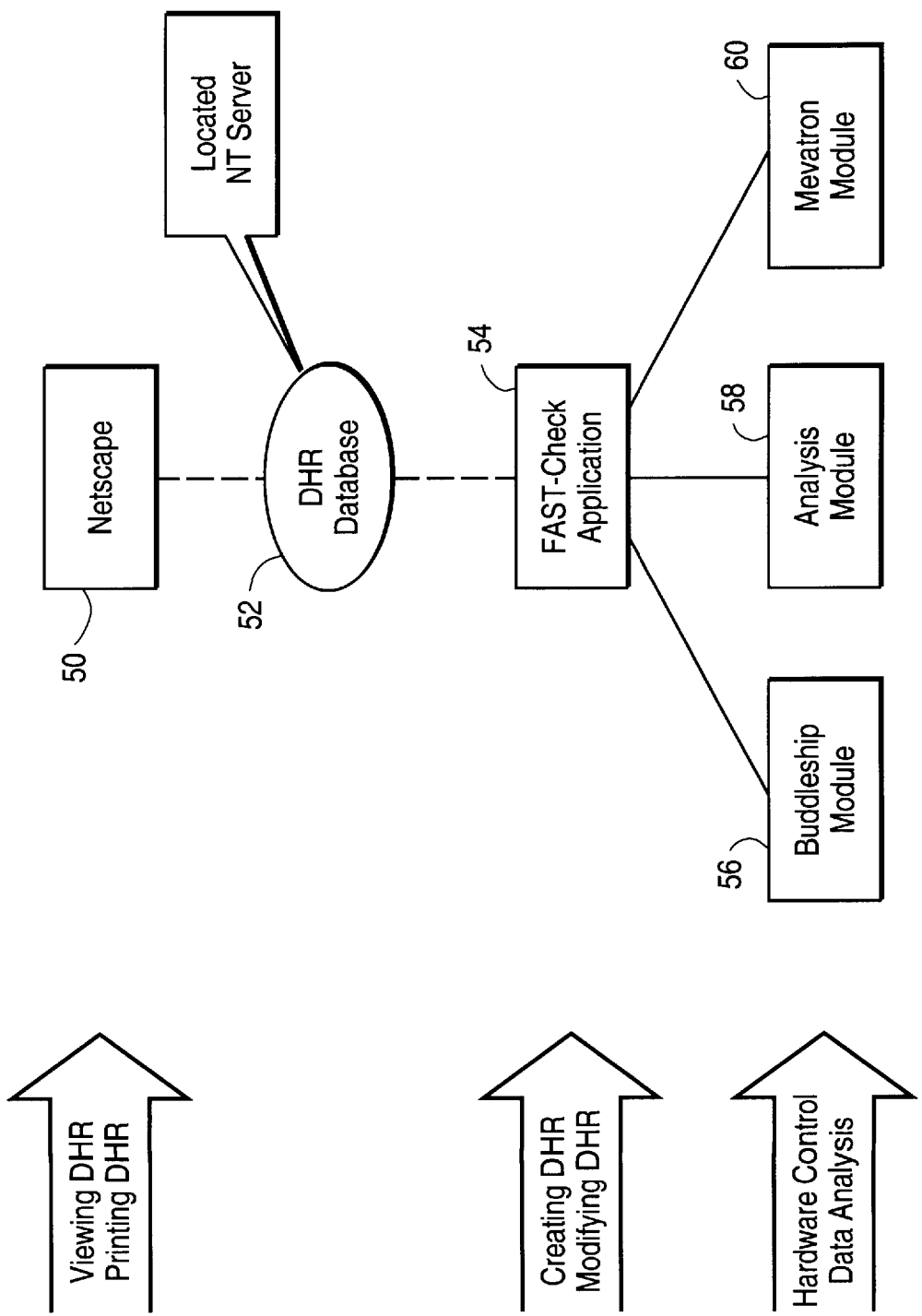
FIG. 2 is a functional block diagram.

FIG. 2 illustrates the division of functionality in the FAST-Check package. The FAST-Check Application is the core of the package. It provides a user interface for data entry and control of the hardware. The layout of the user interface is determined by the document template used. The Buddelship Module provides an interface to the Wellhofer scanning equipment via a serial connection, e.g., using a RS-232 protocol. Additional modules with similar interfaces may be used to allow the FAST-Check package to control other types of hardware. The Analysis Module provides the automated analysis capabilities for the package. The analysis routines currently implemented by this module include those used for beam alignment, scan profiles, off axis ratio, and depth dose. The Mevatron Module provides an interface to the Mevatron via DMIP. The module provides control of treatment setup as well as support for auto-sequencing. The final component is the database, which is used to store the data collected using FAST-Check. An ODBC connection may be used to allow database support for multiple vendors. Each vendor may thus provide an ODBC driver which provides a consistent interface to its database.

A DHR template is used to create new DHRs. Changes to the DHR content are easily accomplished by modifying this template. An Active Server Pages (ASP) file is used to format DHRs for viewing and printing. Changes to the DHR format are easily accomplished by modifying this file. Context sensitive help is also provided by the system to allow the user to access instructions for specific sections of the DHR. Modifications to the help information are easily accomplished by editing, for example, a rich text format (RTF) file used to create the help file. Object Linking and Embedding (OLE) Automation is used as the interface between the software modules to allow the functionality of the modules to be used by many applications, not just the FAST-Check Application. These other applications are not be constrained to a C++ library implementation, but could take advantage of any development effort that can interface via OLE. This provides a generic, clean, and tested interface to the modules. Other applications may include test tools, Visual Basic scripts, and other OLE Containers. ODBC is used to interface to any database from a Microsoft Foundation Class (MFC) application. It provides a generic database independent, interface where the database could later be changed for another without impacting the design. One advantage of using the intranet to provide DHR information is platform independence. The company intranet exists and the client side software is installed on most PCs and workstations. Using server-side scripting to provide Hypertext Markup Language (HTML) formatted DHRs allows changes to be implemented quickly and easily from a centralized location. Using this strategy DHRs may be viewed on line, by multiple users, in remote locations, on different platforms. This is a much more effective solution than distributing and maintaining a platform specific FAST-Check Viewer" to each individual needing access to the DHR.

A Netscape Navigator module 50 may serve as the user interface for viewing and printing DHRs. The System Calibration Web Site provides access to the DHR database 52 and uses internet HTML formatting of the DHR document. The HTML web site commercially available is a purchased module. The FAST-Check Application Software Module 54 will be the primary user interface for FAST-Check data entry and control of automated measurements. It will exist as an application using ODBC to interface to the database, and OLE to interface with the other software modules. The FAST-Check Application will also be an OLE Container application, as some of the functions within will be implemented as OLE controls (OCX).

A scanner (Buddelship) Software Module 56 provides an interface to the Wellhofer Scanning Equipment. It may exist as an OLE control to provide a clean, application independent, high level OLE interface for communicating with the Scanning Equipment. The control will have a minimal user interface.

This module provides the scan analysis capabilities required for the FAST-Check package. It may exist as an OLE control to provide a clean, application independent, high level OLE interface for automated analysis of scan data. The control may have a fully developed, self-contained user interface within the FAST-Check Application. Radiation Therapy Device (Mevatron) Software Module 60 provides an interface to the Mevatron Control Console. It may exist as a stand-alone application to provide a clean, application independent, high level OLE interface for communicating with the Mevatron. The application may run in the background, but still have a minimal user interface.

As described further below, commercially available PC hardware is the underlying structure that supports the goals of the FAST-Check Subsystem. It may support either the Windows NT or Windows 95 operating system, the external interfaces to the NT Server, the Control Console, and the Scanning Equipment, as well as the FAST-Check application and modules. This database contains all the data for the DHR. A Microsoft Access V7.0 database may be used, as described in the implementation below. The FAST-Check Application may use ODBC to connect to this database. ODBC provides a generic, database independent, interface which allows databases from multiple vendors to be supported.

The hardware module may be specified as an Intel based PC hardware platform. A summary of the PC equipment is listed below.

Figure 3:
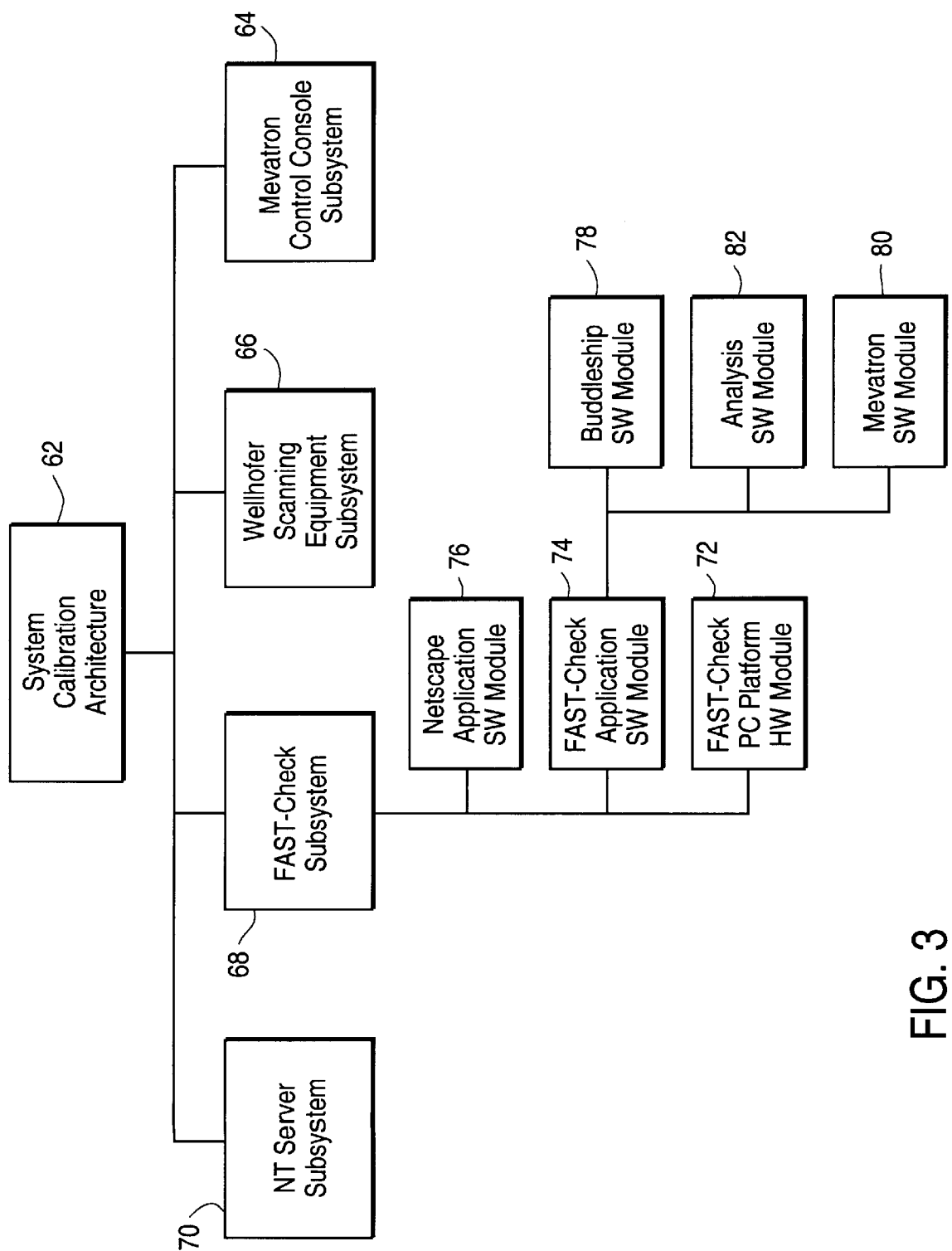
FIG. 3 is a system calibration architecture block diagram.

Functional Requirements:
CPU: Pentium, 133 MHz, 256K, cache, or better
RAM: 32 MB or better
Hard Disk: 500 MB or better
Floppy: 1.44 MB floppy drive
Video: 640×480, 256 colors, or better
Monitor: 14", or larger
Interfaces: Ethernet, 10BaseT
  2 Serial and 1 Parallel I/O ports (RS-232 serial interface, Centronics printer interface)
Keyboard: Standard 101
OS and Network OS: Windows 95 or Windows NT 4.0
  Client for Microsoft Networks installed FIG. 3 shows the system calibration architecture 62 which includes the Mevatron Control Console Subsystem 64, the primary real time controller of the Mevatron that communicates with slave processors within the Mevatron Module 80 software interface. The Control Console 64 and Mevatron Structure 80 will be controlled by the FAST-Check Subsystem via a serial digital Mevatron interface protect (DMIP) connection. They are also capable of standalone operation. The Control Console 64 software exists on a commercially available Radisys board in a hardware tower outside the treatment room at the treatment control station. The Wellhofer Scanning Equipment Subsystem 66 is used to measure the radiation produced by the Mevatron. It is connected to the PC hardware via a serial connection. The Wellhofer Scanning Equipment will be controlled by the FAST-Check Subsystem 68. It is also capable of standalone operation using the Wellhofer software, which also provides analysis capabilities.

The System Calibration Server Subsystem is a Windows NT Server 70 that maintains the DHR template and DHR databases and serves client workstations with data and applications. The server is accessible via the company network. The FAST-Check Subsystem is based on a 32-bit Microsoft operating system and an Intel based PC hardware platform 72. The FAST-Check Application Software Module 74 operates with either Microsoft Windows 95 or Microsoft Windows NT 4.0 or higher. The described personal computer embodiment includes a Netscape application software module 76, i.e., Navigator 3.0 or higher and four software modules developed using Visual C++, based on the Microsoft Foundation Classes (MFC).

Figure 4:
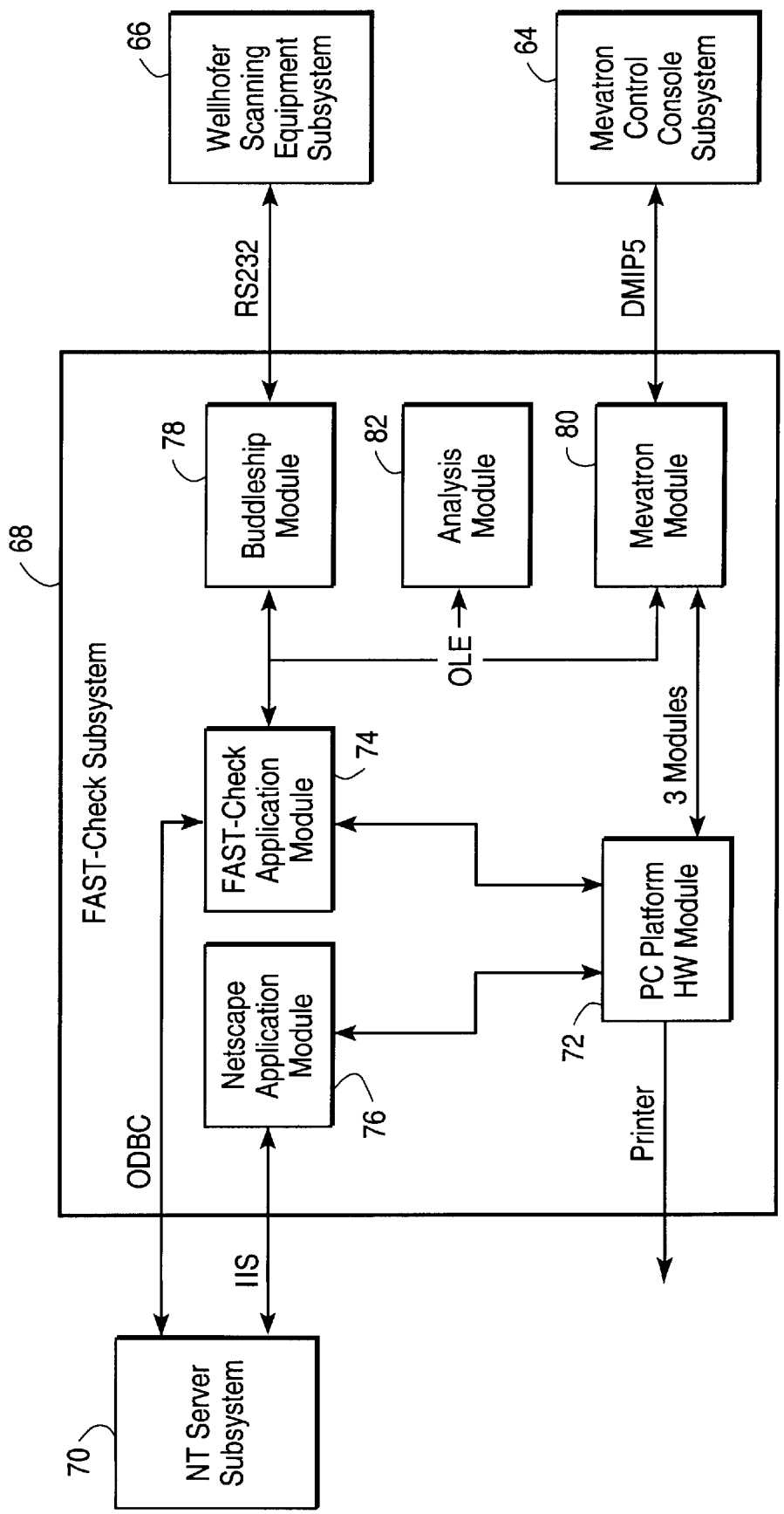
FIG. 4 represents the FAST-Check interface block diagram.

The FAST-Check Interface block diagram of FIG. 4 shows the six (6) modules, their internal interfaces, and their external interfaces to the NT Server 70, Mevatron Control Console 64, and Wellhofer Scanning Equipment 66. The interface to the NT Server may be a standard TCP/IP network connection used to access the data which resides on the server using an Internet Information Server (IIS). The interface to the control console may be the Mevatron interface protocol DMIP 5. The interface to the scanning equipment may be an RS-232 serial link. All the internal software modules interface with the underlying hardware module through the operating system, and interface with the FAST-Check Application module via OLE.

Figure 5:
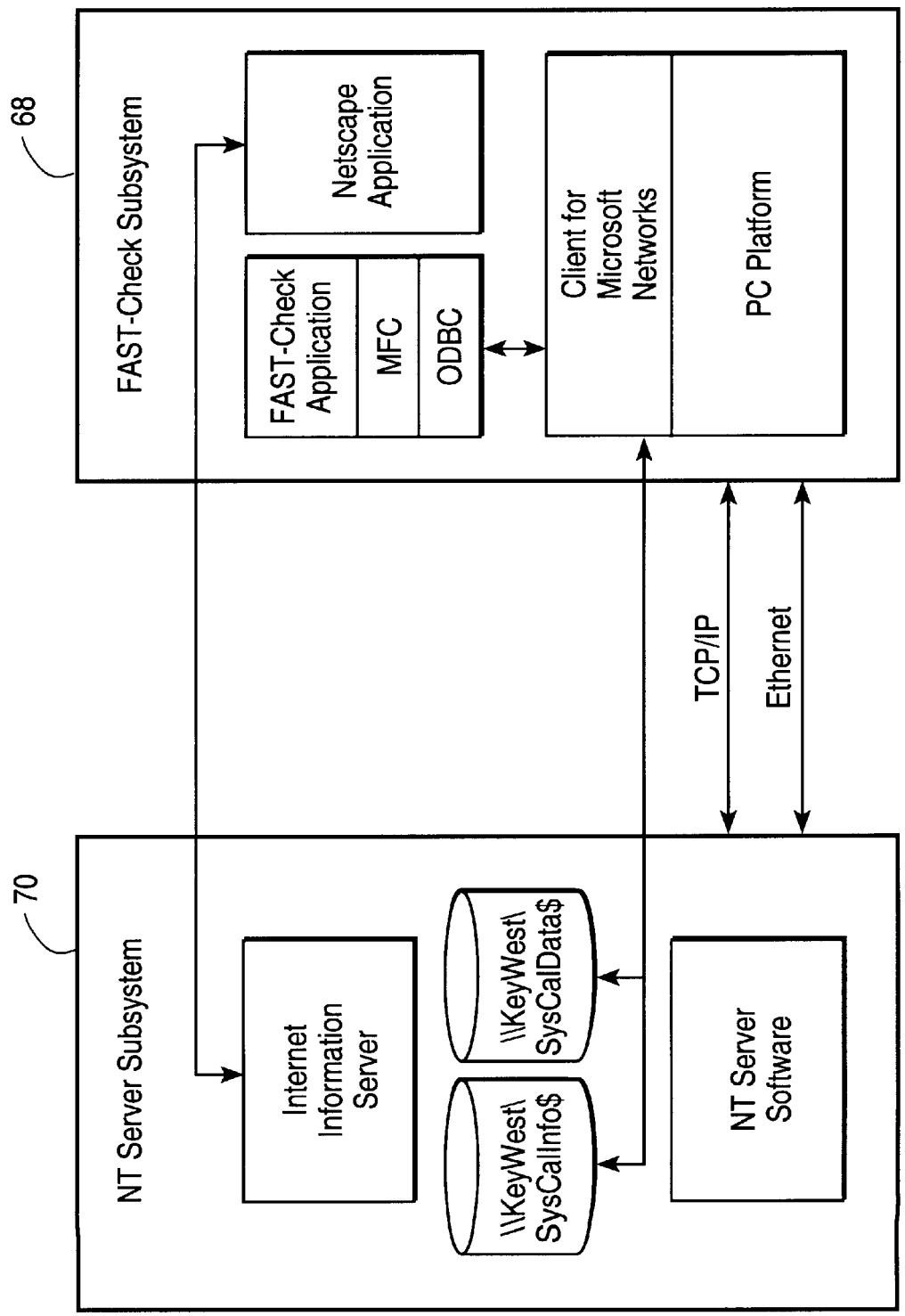
FIG. 5 represents the FAST-Check interface to the NT Server.

The NT Server provides two main functions to the FAST-Check Subsystem as shown in FIG. 5 which illustrates shared, controlled access to the databases residing on the server and an intranet server interface. The database access is achieved via a network connection and ODBC. The intranet server interface is provided by the Internet Information Server package bonded with NT Server 4.0. This interface provides support for Active Server Pages (ASP), allowing the databases residing on the server to be accessed and HTML formatted through server-side scripting (JavaScript). At the lower communications levels all the interaction between the systems occurs using TCP/IP over Ethernet.

Figure 6:
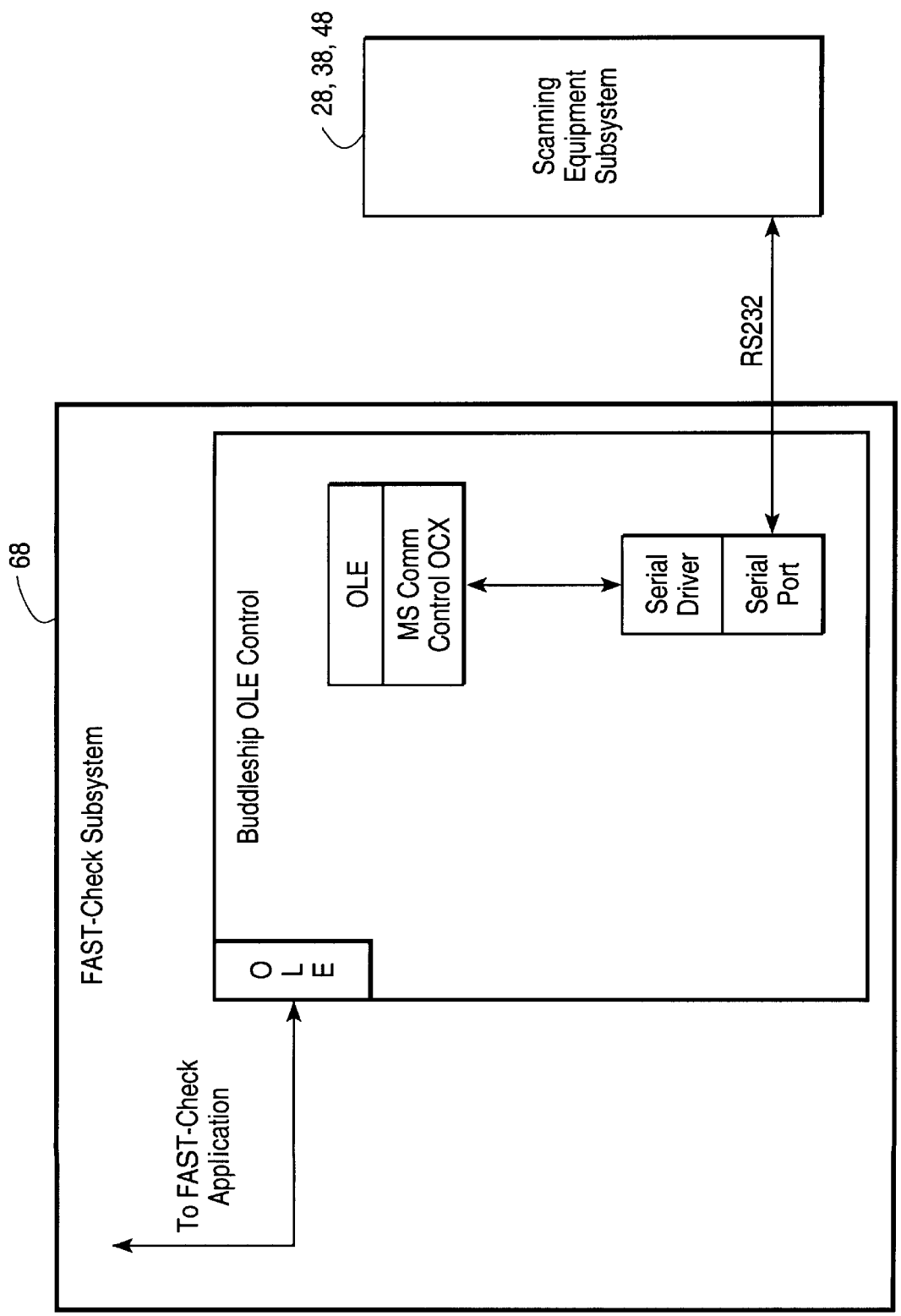
FIG. 6 represents the Buddelship module interface to the scanning equipment.

The Buddelship Module 78 to Scanning Equipment is implemented as an external interface shown in FIG. 6 to the Wellhofer Scanning Equipment Subsystem. This interface is provided in the form of a serial link. The Buddelship Module 78 in the FAST-Check Subsystem is responsible for supporting serial communications to the Scanning Equipment. The operating system provides the serial driver for the serial port and an OLE control (OCX) to support serial communications through the serial driver. The Buddelship Module uses this OCX for the serial communications by providing a container application in which to embed the control. The Buddelship Module is then responsible for implementing appropriate communications over the serial link. The Buddelship Module is implemented as an OLE control.

The Analysis Module follows the high level design concepts of an OLE control, providing the specification for interfaces between objects. OLE Automation is an OLE technology that allows one program to control another by setting or reading properties and invoking methods on them. OLE Controls use this technology to support custom, user defined, methods. An OLE Container "contains" the OLE Control and can expose any of the control's interfaces as its own. The OLE Control extends the basic OLE Automation technology described above by allowing the control to send notifications to its container asynchronously rather than only at the request of the container. Thus the OLE Container can both send requests to and receive notifications from the OLE Control. The Analysis Module adds several dialogs and a toolbar with tool tips to the standard blocks for an OLE Control. Various screen shots discussed below are provided herein in Appendices A through F.

OLE is used to provide a high level, implementation independent interfacing mechanism between the FAST-Check Application module, the Buddelship Module, and the serial communications OCX.

Figure 7:
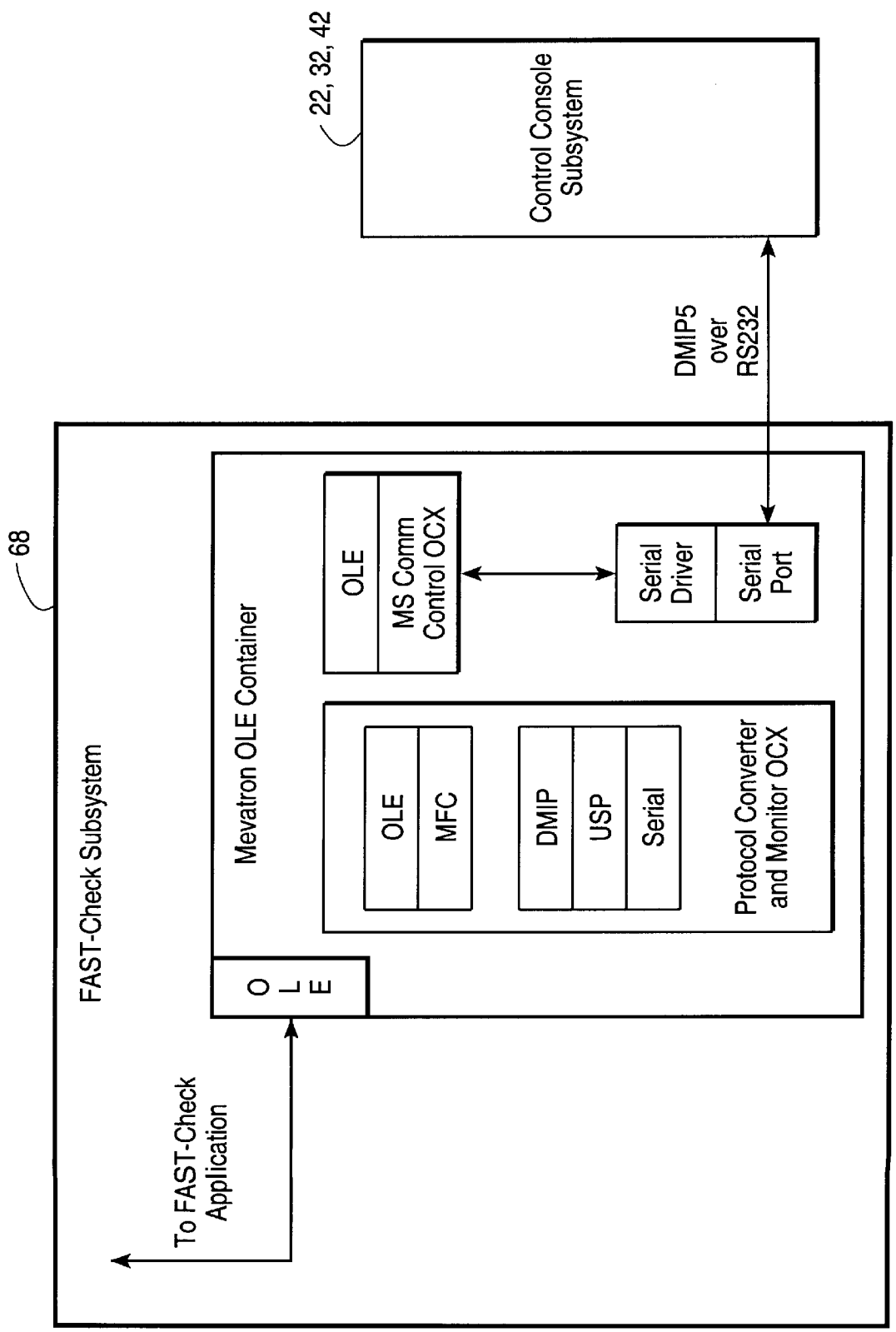
FIG. 7 represents the Mevatron module interface to the control console.

The Mevatron Module 80 Control Console implements an external interface shown in FIG. 7 to the mevatron Control Console Subsystem. For the Control Console this is the Universal Serial Protocol (USP) over RS-232 interface called Digital Mevatron Interface Protocol (DMIP) version 5, which interface is currently in use between the Control Console and the Subsystem. The FAST-Check Subsystem supports DMIP 5 over this existing link to the new 6.2 Control Console. The Mevatron Module 80 in the FAST-Check Subsystem is responsible for supporting DMIP 5 communications to the Control Console. The operating system provides the serial driver for the serial port and an OLE control (OCX) to support serial communications through the serial driver. The Mevatron Module 80 uses this OCX for the serial communications by providing a container application in which to embed the control. The Mevatron Module 80 is then responsible for implementing the layers of communications over the serial link. This responsibility will be handled by another control within the Mevatron Module 80, also called the protocol Converter and Monitor OCX.

An additional external interface may be supported on the FAST-Check Subsystem is a printer interface. The Netscape Application will use the printer interface. Printing is supported by the operating system, providing a printer independent interface, and printer drivers for all applications to use. The FAST-Check Subsystem may use a Hewlett Packard LaserJet 4 or above.

Figure 8:
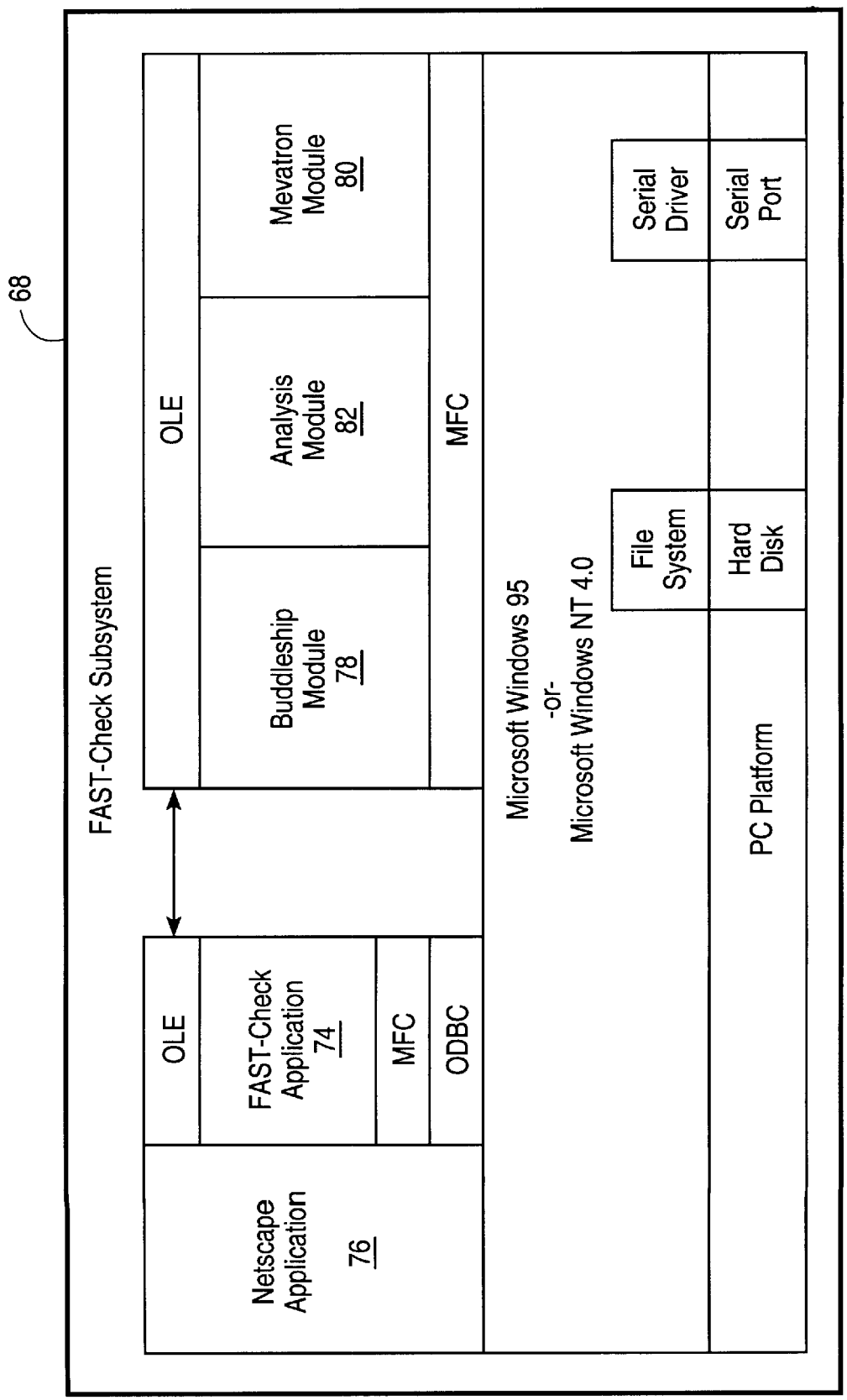
FIG. 8 represents the internal FAST-Check interfaces.

As shown in FIG. 8, the internal interface modules within the FAST-Check Subsystem have two main internal interfaces. All the software modules must interface with the operating system and PC hardware module. In addition, the FAST-Check Application communicates with the Buddelship, Analysis, and Mevatron Modules using OLE. The Netscape Application does not communicate with any of the other software modules directly; it shares a database with the FAST-Check Application. The FAST-Check Application and Buddelship, Analysis, and Mevatron Modules interface to the PC hardware through Microsoft Foundation Class (MFC) and the operating system. The described internal interface may be provided in the Visual C++ development environment. MFC provides the software modules clean interfaces to any underlying operating system functions and hardware (e.g., keyboard, display, communications). At a higher level the FAST-Check Application module communicates with the Buddelship, Analysis, and Mevatron Modules via OLE Automation. OLE is a high level, language independent, interface that can be used between applications under the Microsoft operating systems. This provides the Buddelship, Analysis, and Mevatron Modules the ability to support non-FAST-Check applications with an implementation independence. This high level interface also provides a clean encapsulation of the external communications support provided by the Buddelship and Mevatron Modules for testing and validation purposes.

This Fast-Check Application will be the primary user interface for FAST-Check data entry and control of automated measurements. It will interface with the Buddelship, Analysis and Mevatron software modules using OLE and to the DHR database using ODBC. The following subsections specify the requirements that the FAST-Check Application software module must support. The FAST-Check Application software module shall provide the user interface with data entry and control of automated measurements as specified in the FAST-Check Functional Requirements Specification. The FAST-Check Application software module shall create new DHR databases as required, update and maintain existing DHR databases, and "freeze" DHR databases when DHRs are completed. The FAST-Check Application will automatically notify Document Control via e-mail when a DHR is completed.

The FAST-Check Application software module 74 supports an OLE Automation interface to the Buddelship Module 78 to download and upload scan information to the Scanning Equipment. The FAST-Check Application software 74 module shall support an OLE Automation interface to the Analysis Module 82 to allow automated analysis of scan data to occur. The FAST-Check Application software module 74 shall support an OLE Automation interface to the Mevatron Module 80 to download and upload treatment information to the Control Console. The interface between the FAST-Check Application and Buddelship 78, Analysis 82, and Mevatron 80 Modules may be an asynchronous interface to ensure that the FAST-Check Application module 74 is not blocked while waiting for a response from the modules (or the devices they communicate with.) The FAST-Check Application software module 74 shall support the external interface to the databases residing on the NT Server 70 as described below using a standard TCP/IP network connection and open Database Connectivity (ODBC). The FAST-Check Application software module 74 shall have read and write access to all databases, and shall also have the ability to create and maintain new databases via the network connection.

The FAST-Check Application software module 74 exists as an MFC application developed under Microsoft Visual C+30 . The FAST-Check Application software module shall follow the high level design concepts of an MFC Single Document Interface (SDI) Application. For communications to the database, the FAST-Check Application software module shall use ODBC interfaces for flexibility and future portability. For communications with the Buddelship, Analysis and Mevatron Modules, the FAST-Check Application software module shall use OLE as a high level interface to allow a loose coupling and isolation from serial communication issues. The FAST-Check Application software module shall be an OIE Container to allow some of the sub-modules within to be implemented as OLE controls (OCX).

The FAST-Check Application module 74 follows the high level design concepts of an MFC Single Document Interface (SDI) application. The cornerstone of the Microsoft Foundation Classes (MFC) is the document/view architecture. In a document/view application, the applications data is represented by a document object and views of that data are represented by one or more view objects. The document and view objects work together to process the users input and provide a representation of the resulting data. The Single Document Interface supports just one open document at a time.

FAST-Check extends the SDI framework by providing support for ODBC database access using recordsets, which are rows of data from a given database. FAST-Check's document object contains information about when databases are accessed and by whom. The actual data that is entered is stored in the database (recordset). Therefore, the applications data is actually made up of two types of components, the document object and the recordset objects. The application's views are "pages" from a given database. The database is currently implemented as a Microsoft Access V7.0 database, and each "page" from the database is a table in the Access database.

Figure 9:
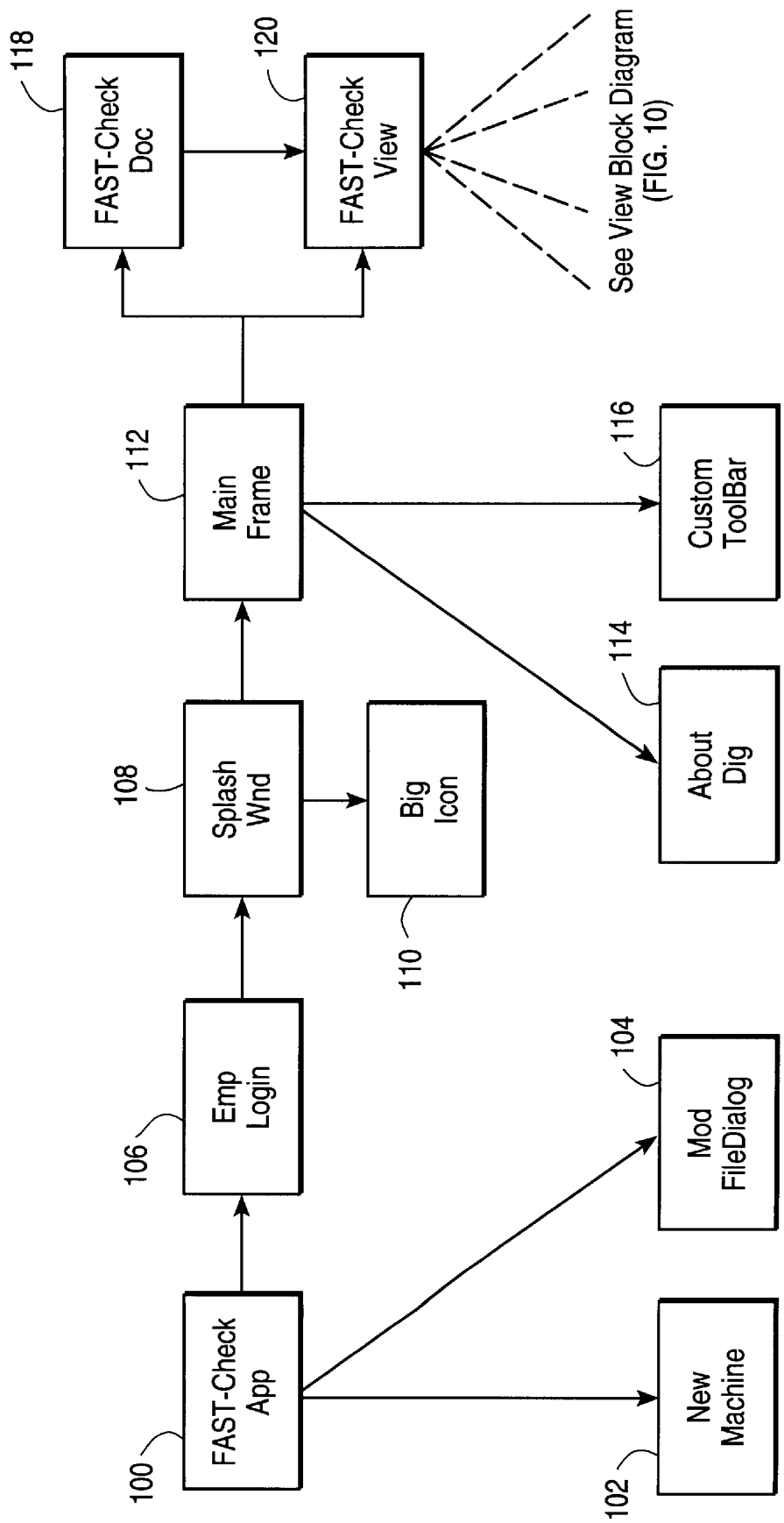
FIG. 9 represents the FAST-Check application block diagram.

Turning now to the Application block diagram of FIG. 9, the FAST-Check Application Block diagram documents the main sequence in which the blocks will be called, as well as identifying interactions between blocks. The standard flow for an SDI application can be identified by considering only the blocks with light gray shadows. In a standard SDI application the "App" block is called first. The "App" block creates the "MainFrame," which is the frame window containing the menu bar, tool bar, etc. for the application. The "MainFrame block creates the "Doc" and "View" blocks, which contain the applications data and a representation of that data. FAST-Check adds "EmpLogin and "SplashWind" to this sequence (see below), which allows a security check to be performed ("Emplogin") prior to actually opening any documents and provides a "splash" window which displays program information while the application is being initialized. The sub-blocks below "App," "SplashWind" and "MainFrame" are used to customize the appearance and behavior of the blocks they are subordinate to. The "View" block also has several sub-blocks, which are diagramed and discussed in the following section. Each block represents a class, and the terms will be used interchangeably in the remainder of this document.

The FAST-Check App 100 contains code that controls the execution of the application. It is based on the MFC class CWinApp, thus it inherits all the functionality of that MFC class. The class member lnitinstance( ) is overridden to call "EmpLogin" and "SplashWind" prior to creating the "MainFrame" class, which then creates the "Doc" and "View" classes. The OnFileNew( ) class member is overridden to call "NewMachine" prior to creating a new document. The OnFileOpen( ) class member is overridden to use a modified file dialog, "ModFileDialog." NewMachine 102 provides the user with a screen to enter configuration information. It is based on the MFC class CDialog, thus it inherits all the functionality of that MFC class. This dialog must be properly filled out prior to creation of a new document. ModFileDialog 104 provides the user with a modified file dialog which limits their ability to change directories and file types. It is based on the MFC class CDialog, thus it inherits all the functionality of that MFC class. This dialog is used for both File-Open and File-Save-As operations. EmpLogin 106 provides the user with a screen to enter a user name and password. It is based on the MFC class CDialog, thus it inherits all the functionality of that MFC class. Actual validation of the user name and password is performed in the lnitinstance( ) member of the "App" object SplashWind 108 provides the user with a splash screen that displays program information. It is based on the MFC class CDialog, thus it inherits all the functionality of that MFC class. This class uses the "Bigicon" class to display a large icon in the dialog. Biglcon 110 is used to display a large icon. It is based on the MFC class CButton, thus it inherits all the functionality of that MFC class. This class is used by the "Splashwind" class. MainFrame 112 provides support for the applications top-level window. It is based on the MFC class CFrameWind, thus it inherits all the functionality of that MFC class. The OnCreate( ) class member is overridden to implement a custom tool bar, "CustomToolBar." AboutDig 114 provides the user with an About Box. It is based on the MFC class CDialog, thus it inherits all the functionality of that MFC class. This dialog displays version information. CustomToolBar 116 provides the user with a modified tool bar. It is based on the MFC class CToolBar, thus it inherits all the functionality of that MFC class. Custom features include displays for employee name and status information. FAST-Check Doc 118 provides support for the document object. It is based on the MFC class CDocument, thus it inherits all the functionality of that MFC class. This class overrides the Serialize( ) class member to store and retrieve application data. It also overrides the OnNewDocument( ), OnOpenDocument( ), OnFileSaveAs( ), and OnCloseDocument( ) class members to update the application data as appropriate. FAST-Check View 120 provides support for the view object. It is based on the MFC class CView, thus it inherits all the functionality of that MFC class. This class overrides the OnCreate( ) class member to provide support for viewing the document "pages" in the database.

Figure 10:
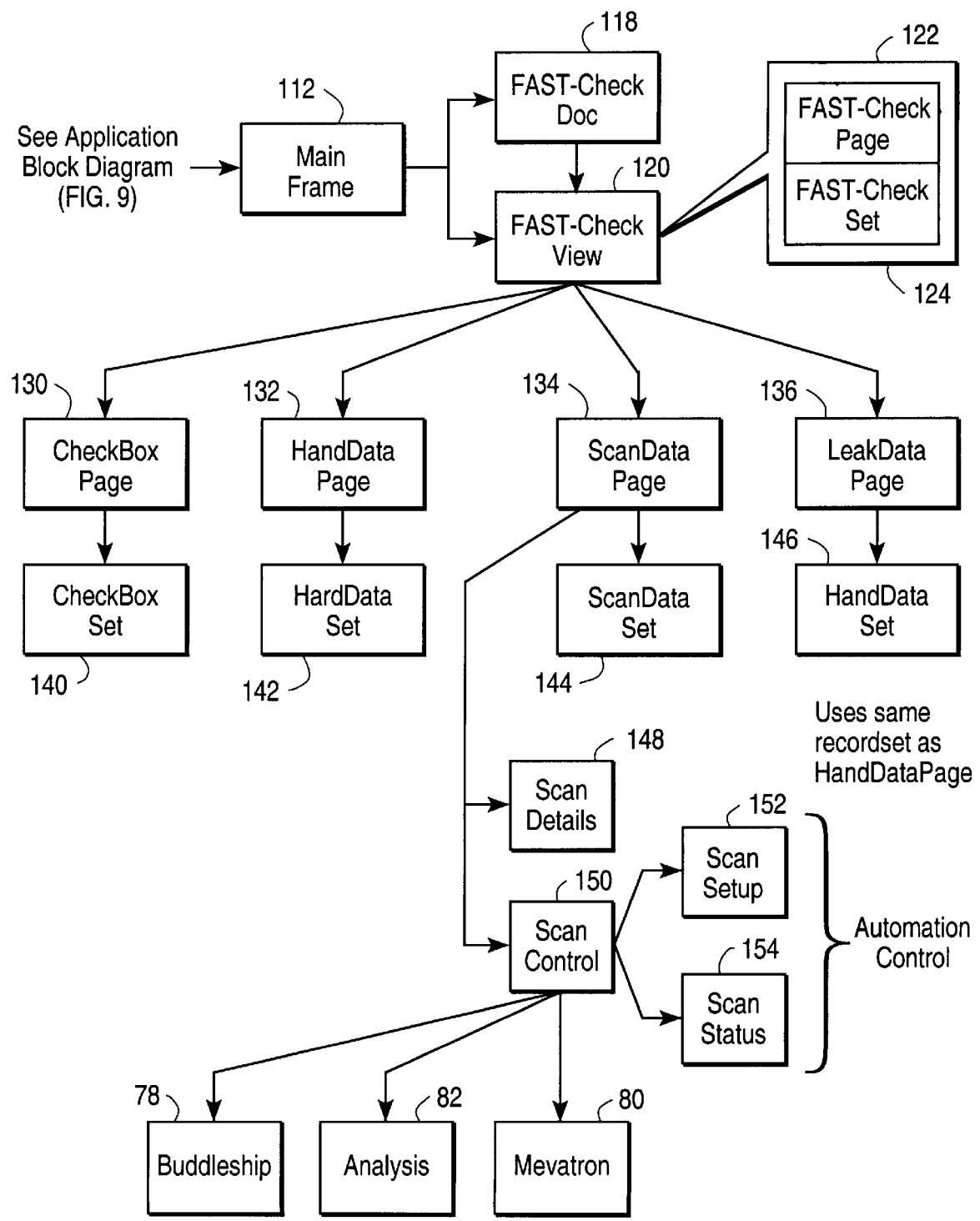
FIG. 10 represents the FAST-Check view block diagram.

The FAST-Check View Block diagram of FIG. 10 documents the types of views available and identifies interactions between blocks. The block that is chosen under the "View" object is determined by the data type for the page. Each page has a recordset associated with it that provides access to the proper "page" in the database. See the following sections for a more complete description of the page types and the automation control screens.

FAST-Check Page 122 is a virtual class, which means that it cannot be initiated as an object itself, but merely serves as a template for the other page types. The virtual class page type is based on the MFC class CDialog, thus it inherits all the functionality of that MFC class. This class provides the following virtual class members: SetTable( ), Update EnergyValues( ), and IsComplete( ). SetTable( ) is used to specify which table to use in the associated recordset. UpdateEnergyValues( ) fills in document specific energy values as required in the item descriptions. IsComplete( ) is used to determine whether a page is complete or not. CheckBoxPage 130, HandDataPage 132, ScanDataPage 134, and LeakDataPage 136 implement the "page" view for the data contained in their associated recordsets. They are based on "FAST-Check Page, thus they inherit all the functionality provided by "FAST-Check Page" (as well as CDialog). The appropriate view is selected based on the page type.

FAST-Check Set 124, including CheckBoxSet 140, HandDataSet 142, ScanDataSet 144 and HandData Set 146 provide access to the data contained in the recordset associated with a page. They are based on the MFC class CRecordset, thus they inherit all the functionality of that MFC class. The "FAST-Check Set" provides access to the "machine" table in the database. The other classes provide access to an appropriate table based on the page they are associated with. ScanDetails 148 provides the user with a screen to manually edit data collected using automated devices. It is based on the MFC class CDialog, thus it inherits all the functionality of that MFC class. This dialog is used with "ScanDataPage and "ScanDataSet". ScanControl 150 provides the user with a screen to control the automated scanning equipment. It is based on the MFC class CDialog, thus it inherits all the functionality of that MFC class. ScanSetup 152 provides the user with a screen to enter custom setup information for automated scanning. It is based on the MFC class CDialog, thus it inherits all the functionality of that MFC class. ScanStatus 154 is used to provide status information for the automated scanning equipment. It is based on the MFC class CDialog, thus it inherits all the functionality of that MFC class. Buddelship 78, Analysis 82 and Mevatron 80 provide support for OLE communication with the appropriate modules as discussed above.

The data type specific pages and recordsets are described as follows: All databases contain a recordset named "master". The "master" recordset must have the following fields (all of type character): [test], [type] and [table]. Each record in the "master" recordset identifies a unique page. The [test] field describes the test being performed. The [test] field will be displayed on the page tab. The [type] field identifies the type of test being performed. The [type] field determines which "Page" and "Set" class will be used (see below). The [table] field identifies which recordset to store the data for the page in. In reference to Appendix A, a sample database is shown with sample tables. The only table name that is required in a database is "master". The other tables exist only because they are defined by master. Table "leakc" is not shown but has the same field structure as table "mic."

The following four types of data are supported:

(1) Checklist Pages—"CheckBoxPage" (Appendix B)

Pages described in the "master" recordset as having [type]="check" will be handled using the "CheckBoxPage" and "CheckBoxSet" classes. The recordset identified by the [table] field must have the following fields; [desc], [init], [date], and [time]. Each record in the recordset identifies a test to be performed, and provides storage for data specific to that test. The "CheckBoxPage" will have a format similar to Appendix B.

(2) Hand Data Pages—"HandDataPage" (Appendix C)

Pages described in the "master" recordset as having [type]="hand" will be handled using the "HandDataPage" and "HandDataSet" classes. The recordset identified by the [table] field must have the following fields: [desc], [init], [date], [time], [data1], [data2], [data3], [data4], [data5], [data6], and [data7]. The number of columns on the page will be determined by the number of non-empty header fields in [data1] through [data7], up to the maximum of seven columns. Each record in the recordset identifies a test to be performed, and provides storage for data specific to that test. The "HandDataPage" will have a format similar to Appendix C.

(3) Data Scan Pages—ScanDataPage" (Appendix D-1,2)

Pages described in the "master" recordset as having [type]="scan" will be handled using the ScanDataPage" and "ScanDataSet" classes. The recordset identified by the [table] field must have the following fields: [desc], [extdesc], [init], [date], [time], [file], [data1], [data2], [data3], [data4], and [data5]. The number of columns on the "ScanDetails" page will be determined by the number of nonempty header fields in [data1] through [data5], up to the maximum of five columns. Each record in the recordset identifies a test to be performed, and provides storage for data specific to that test. The "ScanDataPage" will have a format similar to Appendix D-1 and Appendix D-2.

(4) Leak Data Pages—"LeakDataPage" (Appendix E)

Pages described in the "master" recordset as having [type]="leak" will be handled using the LeakDataPage" and "HandDataSet" classes. The recordset identified by the [table] field must have the following fields: [desc], [init], [date], [time], [data1], [data2], [data3], [data4], [data5], [data 6] and [data7]. Currently the page layout is hard-coded in the program and only table names of "leakc," leakr," and "leakt" (Leakage Crossplane, Radial, and Target respectively) are supported. The "LeakDataPage" will have a format similar to Appendix E.

The automation control screens included with FAST-Check minimize the amount of user supplied information, allowing much better control over how the information is collected and eliminating differences in technique between technicians. The main difference between "Rough Scans" and "Final Scans" is that data collected in the "Rough Scans" mode is not automatically saved. Data collect in the "Final Scans" mode is automatically entered into the document (DHR). Both scanning modes provide scan selection via a tree control similar to the one in Appendix F-1. The "Rough Scans" selection in the tree control provides an opportunity to perform a "Custom Scan," with parameters for start and stop positioning specified as in Appendix F-1. Appendix F-2 shows an analysis of data collected using the automated scanning equipment. The manual analysis buttons in the upper right hand corner of the graph provide the ability to perform custom analysis of data. These buttons are not active in "Final Scans" mode, as standard analysis is automatically performed.

It will be appreciated by those skilled in the art the modifications to the foregoing preferred embodiment may be made in various aspects. The present invention is set forth with particularity in the appended claims. It is deemed that the spirit and scope of that invention encompasses such modifications and alterations to the preferred embodiment as would be apparent to one of ordinary skill in the art and familiar with the teachings of the present application.

APPENDIX A

| master : Table | | |
|---|---|---|
| test | type | table |
| Interlocks (1) | check | interlock1 |
| MLC Data | hand | mlc |
| Beam Alignment | scan | align |
| Leakage Crossplane | leak | leakc |
|  |  |  |

Sample "master" table
NOTE: Tables "interlock1", "mlc", "align", and "leakc" exist only because they are defined in "master"

interlock1 : Table

| desc | init | date | time |
|---|---|---|---|
| \hInterlock and Test Description | Initials | Date |  |
| #40 Water Level |  |  |  |
| Water Pump Turns Off |  |  |  |
| #41 Water Over Temp |  |  |  |
| #43 Water Conductivity |  |  |  |
| #36 Chamber HV |  |  |  |
| #37 Gantry Limit Switch |  |  |  |
| #38 Beamshield (HW) (Sector) |  |  |  |
| #39 Motion Stop PB - Console |  |  |  |
| Motion Stop PB - S31 |  |  |  | mlc : Table

| desc | init | date | time | data1 | data2 | data3 | data4 | data5 | data4 | data7 |
|---|---|---|---|---|---|---|---|---|---|---|
| \hLeaves | Initials | Date |  | -10 CM | 0 CM | 10 CM | 20 CM |  |  |  |
| X1 |  |  |  |  |  |  |  |  |  |  |
| X2 |  |  |  |  |  |  |  |  |  |  |
|  |  |  |  |  |  |  |  |  |  |  | align : Table

| desc | extdesc | Init | date | time | file | data1 | data2 | data3 | data4 | data5 |
|---|---|---|---|---|---|---|---|---|---|---|
| \hFunction | Scan Type | Initials | Date |  | File | Ave Dev |  |  |  |  |
| Spot Position | Inplane |  |  |  |  |  |  |  |  |  |
| Spot Position | Crossplane |  |  |  |  |  |  |  |  |  |
| \\h |  |  |  |  |  | Dose Diff |  |  |  |  |
| Beam Exit Angle | Inplane |  |  |  |  |  |  |  |  |  |
| Beam Exit Angle | Crossplane |  |  |  |  |  |  |  |  |  |
| \\h |  |  |  |  |  | Spot | Angle 60% | Angle 75% | Angle 90% |  |
| Primary Collimator | Inplane |  |  |  |  |  |  |  |  |  |
| Primary Collimator | Crossplane |  |  |  |  |  |  |  |  |  |
| \\h |  |  |  |  |  | Diff -3cm | Diff +3cm |  |  |  |

Sample Database Structure

APPENDIX B

| M1000.dhr - OnlineDHR | | | | | |
|---|---|---|---|---|---|
| File Edit View Help | | | | | |

| ✓ Interlocks (1) | ✓ Interlocks (2) | ✓ Interlocks (3) | ✓ MLC Data | ✓ Beam Alignment | ✓ X-HI Fla ◀ ▶ |
|---|---|---|---|---|---|
| Interlock and Test Description | Initials | Date | ☐ #30 Modulator Incomplete | | |
| ☐ #40 Water Level | | | #46 Hook Stick | N/A | N/A |
| ☐ Water Pump Turns Off | | | ☐ RF Pressure | | |
| ☐ #41 Water Over Temp | | | ☐ #48 Table Not Locked | | |
| ☐ #43 Water Conductivity | | | ☐ #55 Interlock Circuits | | |
| ☐ #36 Chamber HV | | | ☐ #11 Dynamic Steering | | |
| ☐ #37 Gantry Limit Switch | | | ☐ #42 Water Flow | | |
| ☐ #38 Beamshield (HW) (Sector) | | | ☐ #27 High Voltage OC | | |
| ☐ #39 Motion Stop PB - Console | | | ☐ #84 Clock | | |
| ☐ Motion Stop PB - S31 | | | ☐ #83 Warm Up | | |
| ☐ #25 Vacuum Overcurrent | | | | | |
| ☐ #46 Hook Stick | | | #86 Electro Magnet (HW) | N/A | N/A |
| ☐ #44 Air Flow | | | ☐ #47 Bending Magnet (HW) | | |
| ☐ #29 Injector Time Delay | | | | | |

Checklist Screen Shot

APPENDIX C
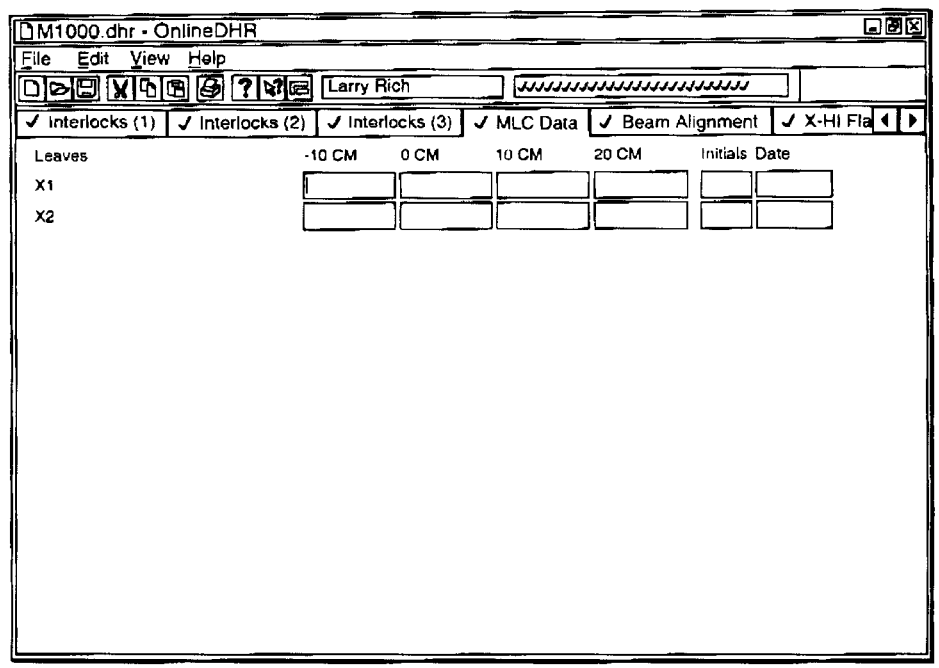
Hand Data Screen Shot

APPENDIX D-1

| D M1000.dhr - OnlineDHR |
|---|
| File  Edit  View  Help |

Toolbar: Larry Rich

Tabs: ✓ Interlocks (1) | ✓ Interlocks (2) | ✓ Interlocks (3) | ✓ MLC Data | ✓ Beam Alignment | ✓ X-HI Fla ◄ ►

| File Ext | Function | Scan Type | Initials | Date | |
|---|---|---|---|---|---|
| | Spot Position | Inplane Crossplane | | | Rough Scans... |
| | Beam Exit Angle | Inplane Crossplane | | | Final Scans... |
| | Primary Collimator | Inplane Crossplane | | | Review Data... |
| | Stability | Inplane | | | |
| | Concentricity 5x5 cm | Inplane Crossplane | | | |
| | Concentricity 35x35 cm | Inplane Crossplane | | | |
| | X-Hi to X-Lo Spot Position | Inplane Crossplane | | | |

Scan Data Screen Shot

APPENDIX D-2

| File | Function | Scan Type | Ave Dev | | | | Initials | Date |
|---|---|---|---|---|---|---|---|---|
| | Spot Position | Inplane | | | | | | |
| | Spot Position | Crossplane | | | | | | |
| | | | Dose Diff | | | | | |
| | Beam Exit Angle | Inplane | | | | | | |
| | Beam Exit Angle | Crossplane | | | | | | |
| | | | Spot | Angle 60% | Angle 75% | Angle 90% | | |
| | Primary Collimator | Inplane | | | | | | |
| | Primary Collimator | Crossplane | | | | | | |
| | | | Diff -3cm | | Diff +3cm | | | |
| | Stability | Inplane | | | | | | |
| | | | Jaw1 | | Jaw2 | | | |
| | Concentricity 5x5 cm | Inplane | | | | | | |
| | Concentricity 5x5 cm | Crossplane | | | | | | |
| | Concentricity 35x35 cm | Inplane | | | | | | |

Scan Details Screen Shot

APPENDIX E
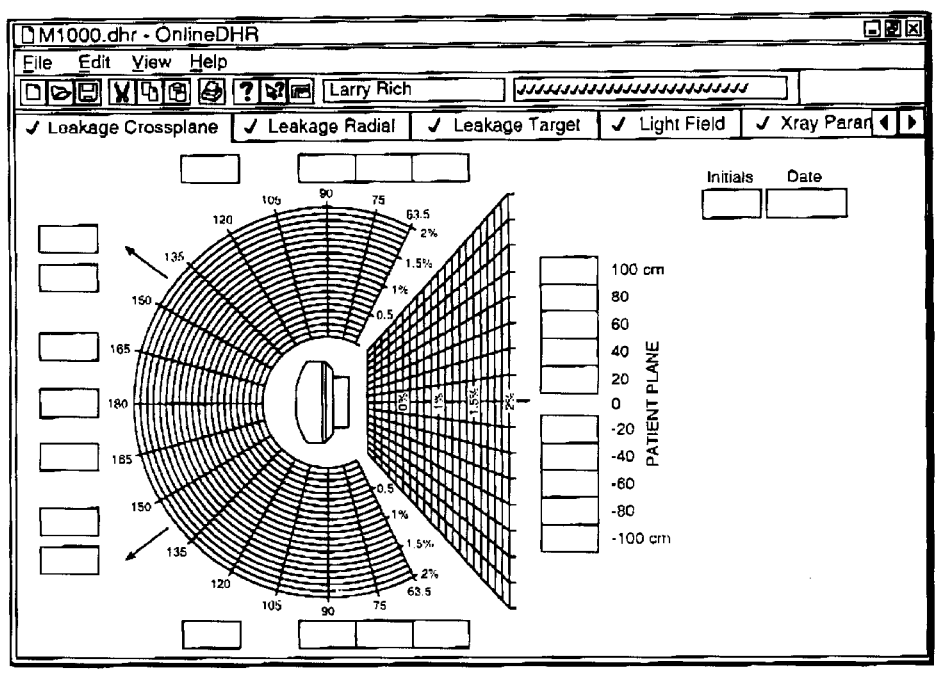
Leak Data Screen Shot

APPENDIX F
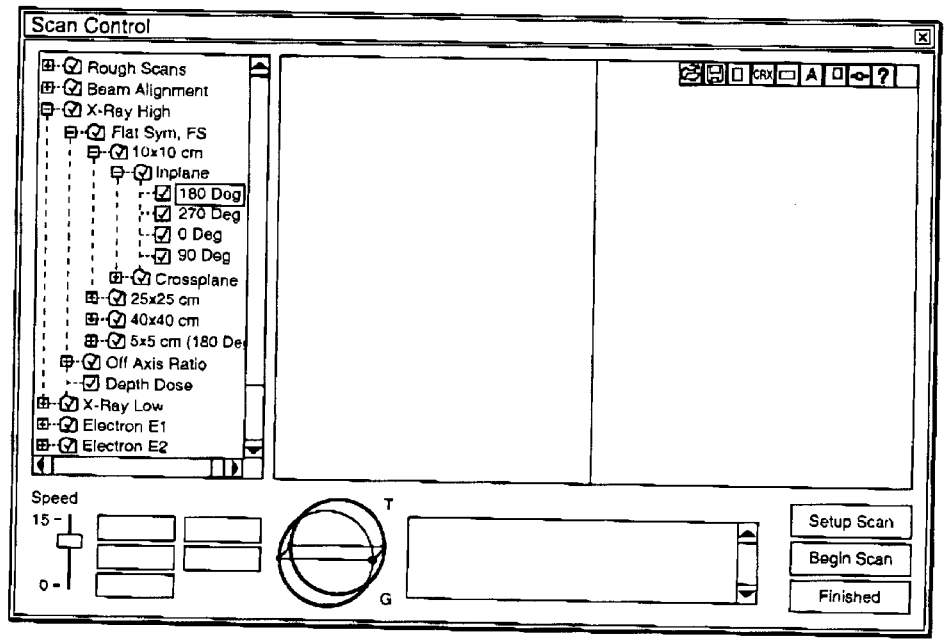
F-1
Automation Controls Screen Shot
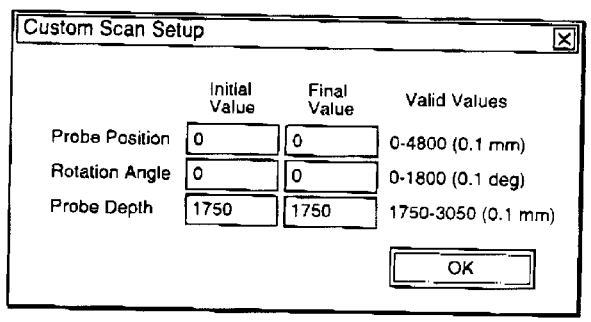
F-2
Custom Scan Screen Shot

What is claimed is:

1. A system for maintaining a network of multiple radiation devices with automated testing, comprising:
    a network interface for coupling the radiation devices to the network through one or more computers;
    a database of device history records for each of the multiple radiation devices;
    a database of device specifications for each of the multiple radiation devices;
    a network server for said device history records database and said device specifications database for use with client applications;
    a dosimetry scanner operable with at least one of the radiation devices; and
    a client user interface provided with the one or more computers in communication with said server via the network and said at least one radiation device and said dosimetry scanner, said radiation device being responsive to said client user interface for undergoing an operation sequence, said dosimetry scanner performing a series of tests on said radiation device being operated in accordance with the series of tests performed by said dosimetry scanner.

2. A system in accordance with claim 1, wherein said client user interface comprises a first communications link to said radiation device for receiving commands for carrying out said operation sequence.

3. A system in accordance with claim 2, wherein said client user interface comprises a second communications link to said dosimetry scanner for receiving commands for performing said series of tests on said radiation device by said dosimetry scanner.

4. A system in accordance with claim 3, wherein said client user interface comprises a dedicated personal computer (PC) employing said first communications link for automatic sequencing of said radiation device.

5. A system in accordance with claim 3, wherein said second communications link comprises a serial interface to said dosimetry scanner.

6. A system in accordance with claim 3, wherein said first and second communications links comprise digital interface protocols for network communications with said radiation device and said dosimetry scanner respectively.

7. A system in accordance with claim 6, wherein said digital interface protocols comprise object linking and embedding (OLE) interfaces.

8. A system in accordance with claim 6, wherein said digital interface protocols comprise a TCP/IP network connection.

9. A system in accordance with claim 3, comprising document templates retrievable by said client user interface for creating new device history records for said radiation devices.

10. A system in accordance with claim 9, wherein said document templates comprise a user interface format including check lists, prompting, semi-automatic or automatic information collection with said radiation device undergoing operation sequences without manual activation of the radiation device by the user, said radiation device being programmed in the operation sequence of the testing commands generated in accordance with a plurality of tests performed by said dosimetry scanner in which said radiation device generates radiation during the performance of at least one of said tests.

11. A system in accordance with claim 10, wherein said network server comprises a system calibration server for comparing said device history records database and said device specifications database for automated analysis of collected information.

12. A system in accordance with claim 11, wherein said databases comprise open database connectivity (ODBC) for database support for multiple vendors.

13. A system in accordance with claim 11, comprising a corporate intranet comprising said server, said network and user interfaces for access and control of collected information.

14. A system in accordance with claim 13, wherein said radiation devices comprise linear accelerator radiation therapy devices.

15. A system in accordance with claim 14, wherein said operation sequence of said radiation therapy devices comprise analysis routines for calibration including beam alignment, interlocks, scan profiles, off-axis ratio or depth dose.

16. A system for automated specification testing and checking of a network of multiple radiation devices, comprising:
    means for coupling the radiation devices to the network;
    means for storing device history records for each of the multiple radiation devices;
    means for storing device specifications for each of the multiple radiation devices;
    means for maintaining the device history records and the device specifications in plural databases on a system calibration server for use with a client user interface;
    means for operating a dosimetry scanner with at least one of the radiation devices via the network; and
    means for communicating with the system calibration server and the at least one radiation device and the dosimetry scanner via the network, the radiation device being responsive to the client user interface for undergoing an operation sequence, the dosimetry scanner performing a series of tests on the radiation device being operated in accordance with the series of tests performed by the dosimetry scanner.

17. A system in accordance with claim 16, comprising document templates retrievable with the client user interface for creating the device history records for the radiation devices, the document templates providing a user interface format including check lists, prompting, semi-automatic or automatic information collection with the radiation device undergoing operation sequences without manual activation of the radiation device by the user.

18. A system in accordance with claim 17, comprising means for programming the radiation device in the operation sequence of the testing commands generated in accordance with a plurality of tests performed by said dosimetry scanner in which said radiation device generates radiation during the performance of at least one of said tests.

19. A method of automatically testing and calibrating a network of multiple radiation devices, comprising the steps of:
    coupling the radiation devices to the network;
    storing device history records for each of the multiple radiation devices;
    storing device specifications for each of the multiple radiation devices;
    providing a system calibration server for maintaining the device history records and the device specifications in plural databases for use with a client user interface;

operating a dosimetry scanner with at least one of the radiation devices via the network; and communicating with the system calibration server and the at least one radiation device and the dosimetry scanner via the network, the radiation device being responsive to the client user interface for undergoing an operation sequence, the dosimetry scanner performing a series of tests on the radiation device being operated in accordance with the series of tests performed by the dosimetry scanner.

20. A method in accordance with claim 19, comprising the steps of retrieving document templates with the client user interface and creating the device history records for the radiation devices, the document templates providing a user interface format including check lists, prompting, semi-automatic or automatic information collection with the radiation device undergoing operation sequences without manual activation of the radiation device by the user.

* * * * *